United States Patent [19]

Henkes et al.

[11] Patent Number: 4,936,680
[45] Date of Patent: Jun. 26, 1990

[54] METHOD OF, AND APPARATUS FOR, EDGE ENHANCEMENT OF FINGERPRINT MINUTIA

[75] Inventors: John L. Henkes, Latham; Daniel D. Harrison, Delanson, both of N.Y.

[73] Assignee: General Electric Company, Schenectady, N.Y.

[21] Appl. No.: 332,069

[22] Filed: Apr. 3, 1989

[51] Int. Cl.$^5$ ............................................. G06K 9/20
[52] U.S. Cl. ...................................... 356/71; 356/369; 382/4
[58] Field of Search ...................... 356/71, 369; 382/4, 382/5

[56] References Cited

U.S. PATENT DOCUMENTS 4,160,237  7/1979  McMahon ..................... 356/369 X
4,385,831  5/1983  Ruell .................................. 382/4 X Primary Examiner—Vincent P. McGraw
Attorney, Agent, or Firm—Geoffrey H. Krauss; James C. Davis, Jr.; Marvin Synder

[57] ABSTRACT

A method for enhancement of edge detail in fingerprint minutia first illuminates the finger with light passing through a polarizer in a first direction with respect to the polarization plane, for at least a portion of one rotation of the light source/polarizer about an optical axis generally perpendicular to the finger. The light reflected from the finger is converted to video data during at least a selected part of the rotation and the first set of video data is stored in a first storage means register. The illuminating, converting and storing steps are then repeated with light from a second direction, substantially orthogonal the first direction, illuminating the finger, and with a second set of video data, (for at least the same part of another rotation) being stored in a second register. Arithmetically processing of the video data in the first and second storage registers is used to obtain a video output signal in which image edge detail data has been enhanced with respect to edge detail data obtainable from either the first and second sets of video data.

15 Claims, 2 Drawing Sheets

METHOD OF, AND APPARATUS FOR, EDGE ENHANCEMENT OF FINGERPRINT MINUTIA

BACKGROUND OF THE INVENTION

The present invention relates to methods of, and apparatus for identifying personnel by fingerprint minutia and, more particularly, to a novel method and apparatus for utilizing images of different frequency content, obtained with light polarized in first and second substantially orthogonal directions, to enhance fingerprint minutia edge detail.

Personnel identification by recognition of fingerprint detail is highly desirable under certain circumstances. Contactless detection of fingerprint detail by optical imaging is, however, normally quite difficult due to the barely different reflective properties of the ridges and valleys of the finger tissue. The resulting contrast is often only slightly greater than the image noise, creating great difficulty in minutia recognition. Thus, video imaging is not easily accomplished by the so-called "frustrated total internal reflection" method, in which the finger is pressed against a three-sided transparent prism; the finger is illuminated by a light source directed upon a prism side other than that side against which the finger is pressed, and the image is collected from the remaining prism side. Total internal reflection is frustrated when skin tissue contacts the glass, so that a bright image of the print is seen against a dark background. This method suffers from many contact-related problems so that the quality of the resultant image is acceptable only for a narrow range of finger temperature, dryness and cleanliness. A contactless method, and especially one with relatively high edge detail, is highly desirable.

BRIEF SUMMARY OF THE INVENTION

In accordance with the invention, a method for enhancement of edge detail in fingerprint minutia utilizes the steps of: illuminating the finger with light passing through a polarizer from a first direction with respect to the polarization plane, for at least a portion of one rotation of the light source/polarizer about an optical axis generally perpendicular to the finger; converting light reflected from the finger to video data during at least a selected part of said rotation; storing the video data in a first storage means; repeating the illuminating, converting and storing steps with light from a second direction, substantially orthogonal to said first direction, to store in a second storage means other video data for at least the same part of another rotation; and arithmetically processing the video data in the first and second storage means to obtain a video output signal in which image edge-detail data has been enhanced with respect to edge-detail data obtainable with either the video data or the other video data alone.

In a presently preferred embodiment, the first set of data is acquired with the light sources substantially perpendicularly disposed to the polarization plane, and the second data set is acquired with substantially parallel disposition. Data set subtraction is utilized to obtain the edge-enhanced output signal.

Accordingly, it is one object of the present invention to provide a novel method for providing a video signal defining edge-enhanced characteristic minutia of a fingerprint.

This and other objects of the present invention will become apparent upon a reading of the following detailed description, when considered in conjunction with the associated drawings.

DETAILED DESCRIPTION OF THE INVENTION

Figure 1:
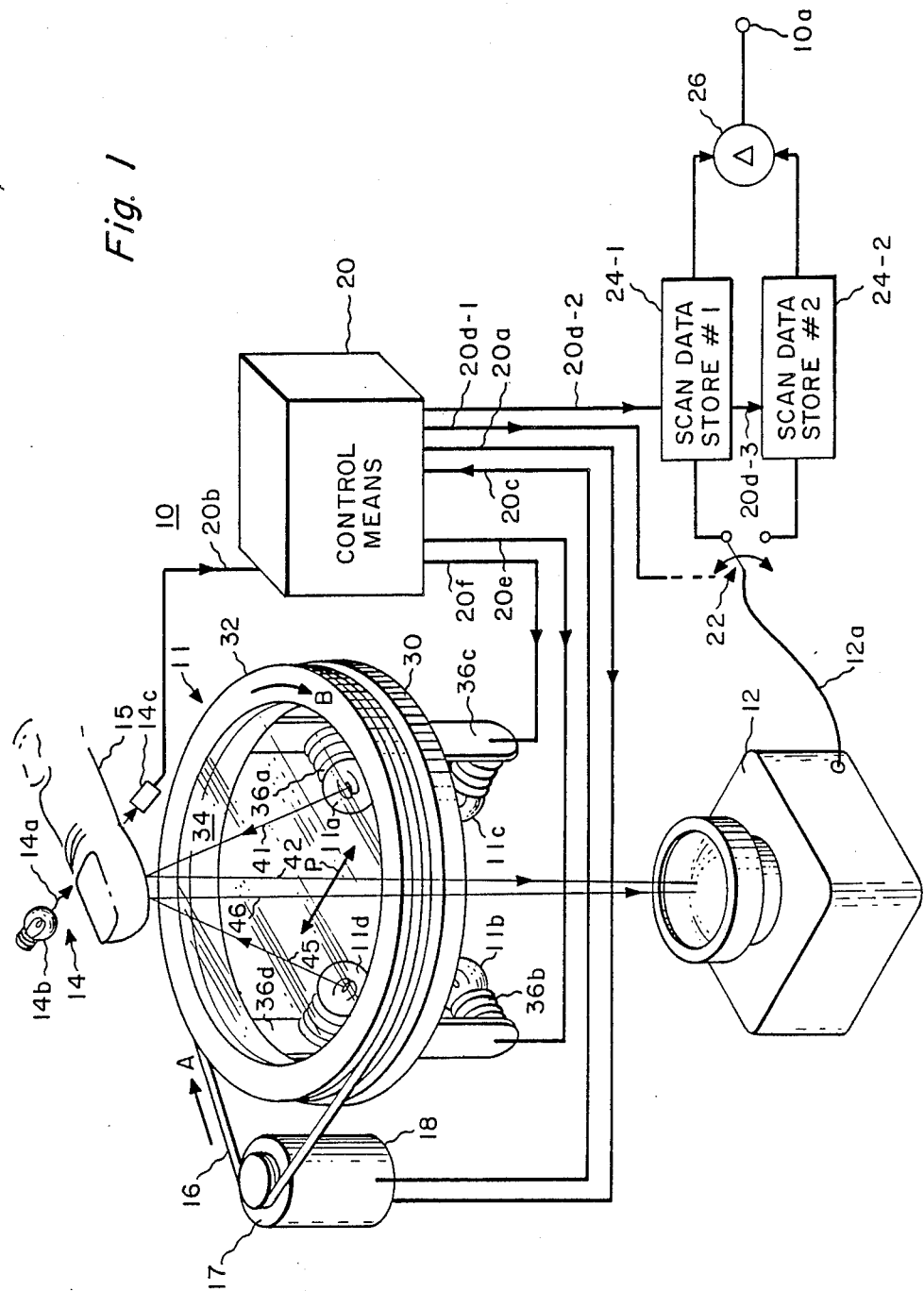
FIG. 1 is a perspective view of apparatus for carrying out the method of the present invention.
Figure 1A:
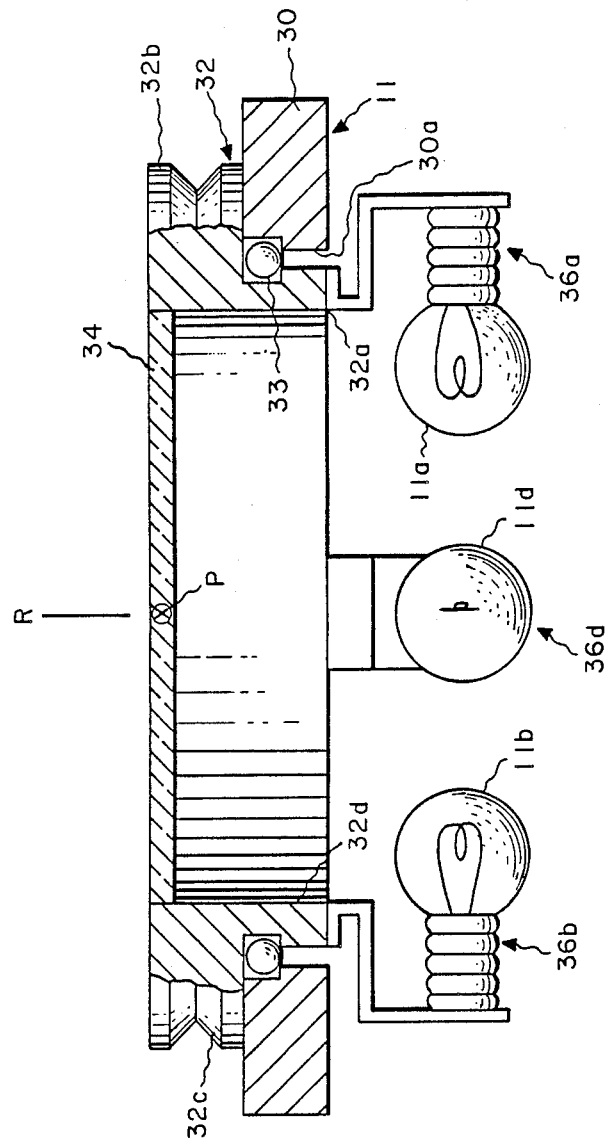
FIG. 1a is a sectional view through the rotating polarizer assembly.

Referring to both figures, an apparatus 10 for providing edge-enhanced, high contrast video signals of fingerprint minutia utilizes a polarizer assembly 11 for providing to a video camera means 12 polarized light reflected from the ridges and valleys of a finger 14 having a fingerprint to be characterized. Polarizer assembly 11 is driven by a belt means 16, engaged by a pulley assembly 17 mounted upon an electric motor 18 and the like. The rotation of motor 18 is enabled by a drive signal from a first output 20a of a control means 20, response to a second input 20b receiving a signal from an initiation means 14 for sensing (as by breakage of a light beam 14a between a source 14b and a sensor means 14c) that a finger 15 has been positioned above assembly 11. The motor provides a signal to a first input 20c of control means 20 to control, via a second output 20d-1, the position of a video signal switching means 22, for switching the video camera data output 12a signal between first and second scan data storage means 24-1 and 24-2; signal storage in means 24-1 or 24-2 is respectively controlled by the energization of one or the other of control means output 20d-2 or 20d-3. The pair of scan storage means is followed by a single subtraction means 26 for providing a difference signal at apparatus output 10a. Control means 20 also has third and fourth outputs 20e and 20f for energizing one or the other of light source 11a/11b or 11c/11d pairs.

Polarizer assembly 11 comprises a fixed base member having a substantially circular aperture 30a therein. An annular member 32 has a lower portion 32a which extends through fixed member aperture 30a and is mounted for free rotation therein, as by means of a ball bearing race 33 and the like, and about rotational axis R. An upper portion 32b of the rotatable member is of larger diameter than the fixed member aperture 30a diameter, and has a suitable formation 32c, such as a V-groove and the like, to frictionally receive belt means 16. Thus, as belt means 16 is moved in the direction of arrow A responsive to clockwise rotation of pulley 17 by motor 18, rotatable member 32 is also driven in the clockwise direction, as shown by arrow B (FIG. 1). Rotatable member 32 has an aperture 32d formed completely therethrough; a planar optical polarizer 34 is mounted therein. Polarizer 34 has a polarization vector P which forms a so-called polarization plane with the axis R. It will be seen that as member 32 is rotated, the polarization plane is also rotated. Dependent from rotatable member lower portion 32a are two pair of light-source mounting means 36, such as a first pair of diametrically-opposed lamp sockets 36a and 36b, and a second diametrically-opposed pair of lamp sockets 36c and 36d. Each lamp socket pair 36a/36b or 36c/36d is energized separately by mutually-exclusive outputs 20e and 20f of control means 20. Advantageously, a first pair of light sources (e.g. sources 11a/11b) are mounted along a first line substantially perpendicularly to the polarization plane (i.e. that plane passing perpendicularly through axis R and through the plane of member 34), and a second pair (e.g. sources 11c/11d) are mounted along a second line substantially parallel to the polarization plane and in a plane passing through the first pair and parallel to member 34; thus the light sources maintain equal angles of incidence with the polarizer and a fixed relationship with the polarization vector during rotation of the polarization member 34. Sources 11 may be wide-spectrum sources (such as light bulbs) or narrow-spectrum sources (such as laser diode monochromatic emitters).

In operation, control means 20 energizes output 20a when finger 15 has entered the space above polarizer assembly 11, and is situated in the proper image plane to activate means 14. Simultaneously, a first light-source-energizing output 20e is enabled, and sockets 36a/36b receive electrical power, causing light to be emitted by sources 11a/11b. This first pair of light sources is located substantially perpendicular to the polarization plane (since a line connecting the two sources is substantially at right angles to polarization vector P) and, while not in the camera view, illuminate finger 15 at a shallow angle through polarization member 34. With the illuminating lamp pair oriented 90° to the polarization vector, the tissue ridge tops give a bright spectral reflection, since Brewster's law causes polarization to be maintained for this angle of illuminating and reflected light. On the other hand, tissue valleys appear to depolarize the incident light (e.g. incident light ray 41) and thus a reflected ray 42 has a very much lower amplitude when reflected from a tissue valley, with respect to the amplitude of light reflected from a tissue ridge; a high ridge-to-valley contrast video signal is created. This high-contrast signal has a relatively large high-frequency content. While the high contrast signal is being obtained during a rotation of member 32, control means 20 also energizes output 20d-1 to cause video switching means 22 to connect the camera output 12a to the input of the first scanned data storage means 24-1. The video data to be stored is acquired in each of at least one video frame each taken at different angles of rotation of the polarizer 11. If the polarizer assembly 11 rotates sufficiently slowly so that material artifacts are not introduced in the time T for one frame (e.g. a sixty-frame-per-second rate has T=1/60 second; if the speed of rotation is, say 30 rpm, then one frame occurs during rotation through only 3°, a very small angle) then motor 18 can be a continuously-running unit; otherwise, motor 18 may be a stepping motor, of properly selected step size, and synchronized with the storage means enable signals on output 20d-2 or 20d-3. In either case, the control means enables output 20d-2 to sequentially store the video data from each sequential one of the at least one frames scanned as the polarizer rotates through the desired part of at least one revolution. Thus, storage means 24-1 contains high contrast data characterizing the fingerprint for at least a selected portion of one revolution of the planar polarizer.

After at least the selected portion of one rotation of member 32 occurs, the control means energizes the other pair of light sockets, as by de-energizing output 20e and energizing the remaining output 20f, to provide electrical power light sources 11c and 11d which are substantially in the polarization plane (i.e. a line between these sources is parallel to polarization vector P). Substantially the same illumination angle and intensity are provided by either pair of light sources 11. Responsive to the rotation position indication signals received at input 20c, the control means causes the video signals from at least that same rotational portion of the next rotation to be stored in the second scan data storage means 24-2. That is, the control means first "sorts" the images, by waiting for the polarizer assembly 11 to rotate through 90° so that the newly-activated sources 11c/11d are positioned at the same starting locations as were sources 11a/11b at the start of their rotation; then, output 20d-3 is enabled, to enable storage of each of the frames of video data obtained with "parallel" illumination. The switching output 20d-1 is reversed during the 90° pre-start time interval, so that the storage means 24-2 input is connected to video output 12a by the time storage in means #2 begins. The ridge and valley tissue in this case appear to reflect light equally well and produce an image which has relatively low contrast and low frequency content, especially as compared to the high frequency content image formed with the light source-perpendicular-to-polarization vector condition.

The alternate images of high frequency content and low frequency content are now stored in respective storage means 24-1 and 24-2, and can be read therefrom, in manner well known to the data storage arts, to have the low frequency content information subtracted from the high frequency content information, in subtraction means 26, so that an output data set contains pixel-by-pixel data of an edge-enhanced image from which fingerprint minutia can be extracted and analyzed.

While one presently preferred embodiment of our novel method of, and apparatus for, edge enhancement of fingerprint minutia is described herein, many modifications and variations will now become apparent to those skilled in the art. For example, the video means 12 can be set up to remain open and integrate the totality of photons reflected from the finger during the entire desired rotation portion, to compile an entire finger picture in one "frame"; this can be done for both the high and low contrast "frames", prior to subtraction. It is our intent, therefore, to be limited only by the scope of the appending claims and not by the specific details and instrumentalities provided by way of explanation of the presently preferred embodiment described herein.

What we claim is:

1. A method for enhancement of edge detail in fingerprint minutia, comprising the steps of:
    (a) illuminating the finger with light passing through a polarizer from a first direction with respect to a plane of a polarization vector, during at least a portion of one rotation of the polarization vector about an optical axis generally perpendicular to the finger;
    (b) converting light reflected from the finger to video data during at least a desired part of the rotation portion;
    (c) storing a first set of video data, for at least the desired rotation part;
    (d) repeating steps (a)-(c) with light from said first direction passing through the polarizer now rotated to have the polarization vector in a second direction, substantially perpendicular to the first direction, to store a second set of video data, for at least the desired part of another rotation; and
    (e) arithmetically processing the first and second sets of video data to obtain an output video signal with image edge detail enhanced with respect to the edge detail obtainable from only one of the first and second video data sets alone.

2. The method of claim 1, wherein step (a) includes the step of aligning the first direction to be substantially perpendicular to the polarization vector of the polarizer; and step (d) includes the step of aligning the second direction to be substantially parallel to the polarization vector of the polarizer.

3. The method of claim 2, wherein step (a) and the repetition thereof in step (d) are performed for at least a selected portion of one rotation of the polarized light source about an optical axis generally perpendicular to the finger; and step (c) and the repetition thereof in step (d) are performed for at least a common part of the selected rotation portion.

4. The method of claim 1, wherein step (e) includes the step of subtracting the second video data set from the first video data set.

5. The method of claim 4, wherein step (a) includes the step of aligning the fist direction to be substantially perpendicular to the polarization vector of the polarizer; and step (d) includes the step of aligning the second direction to be substantially parallel to the polarization vector of the polarizer.

6. The method of claim 5, wherein step (a) and the repetition thereof in step (d) are performed for at least a selected portion of one rotation of the polarized light source about an optical axis generally perpendicular to the finger; and step (c) and the repetition thereof in step (d) are performed for at least a common part of the selected rotation portion.

7. The method of claim 1, further comprising the step of sensing the placement of a finger in a selected volume adjacent the polarizer to cause steps (a)–(e) to be performed.

8. Apparatus for enhancing edge detail of minutia in a print of a finger, comprising:
   a polarizer having a polarization vector;
   means for controllably rotating the polarizer about an optical axis passing through the polarizer;
   means for providing a first source of light impingent upon said finger after passing through the polarizer in a first direction, substantially perpendicular to said polarization vector;
   means for providing a second source of light impingent upon said finger after passing through the polarizer in a second direction, substantially parallel to said polarization vector;
   means for converting light reflected from said finger to video data; and
   means for causing a first set of video data, obtained responsive to light from said first light providing means being received by said converting means, during at least a selected part of a rotation of said polarizer, and a second set of video data, obtained responsive to light from said second light providing means being received by said converting means, during at least the same selected part of another rotation of said polarizer, to be arithmetically processed to obtain an output video signal with image edge detail enhanced with respect to the edge detail obtainable from only one of the first and second video data sets alone.

9. The apparatus of claim 8, wherein said causing means includes: first and second means each for storing one of said first and second set of video data; and control means for causing a different one of said data sets to be stored in each of said storing means.

10. The apparatus of claim 9, wherein said control means includes means for switching the video data from the converting means to the first storage means if the first light-providing means is energized and to the second storage means if the second light-providing means is energized.

11. The apparatus of claim 10, further comprising means for subtracting the second video data set from the first video data set to obtain the output video signal.

12. The apparatus of claim 8, wherein said rotating means includes: a fixed member having an aperture therethrough; a moveable member having another aperture therethrough and in which said polarizer is mounted; and means for rotatably positioning said moveable member with respect to said fixed member and with said aperture and said another aperture in optical alignment.

13. The apparatus of claim 12, wherein said first and second light source means are mounted at fixed positions on the moveable member.

14. The apparatus of claim 13, wherein each of said first and second light source means includes a pair of light-providing elements mounted in diametrically-opposed locations about said another aperture.

15. The apparatus of claim 14, wherein a line between the light-providing elements of the first means is substantially perpendicular to the polarization vector, and aline between the light-providing elements of the second means is substantially parallel to the polarization vector.

* * * * *